United States Patent [19]
Hochmair et al.

[11] Patent Number: 5,876,443
[45] Date of Patent: *Mar. 2, 1999

[54] STRUCTURE, METHOD OF USE, AND METHOD OF MANUFACTURE OF AN IMPLANTED HEARING PROSTHESIS

[75] Inventors: Ingeborg Hochmair; Erwin Hochmair, both of Axams, Austria

[73] Assignee: Med-El Elektromedizinisch Gerate Ges.m.b.H., Innsbruck, Austria

[ * ] Notice: This patent issued on a continued prosecution application filed under 37 CFR 1.53(d), and is subject to the twenty year patent term provisions of 35 U.S.C. 154(a)(2).

[21] Appl. No.: 807,038

[22] Filed: Feb. 26, 1997

Related U.S. Application Data

[60] Provisional application No. 60/012,261 Feb. 26, 1996.
[51] Int. Cl.$^6$ ............................................ A61F 2/18
[52] U.S. Cl. ................................ 623/10; 607/57; 607/137
[58] Field of Search ................................ 623/10; 607/55, 607/56, 57, 116, 137

[56] References Cited

U.S. PATENT DOCUMENTS

| 4,284,856 | 8/1981 | Hochmair et al. | 607/66 X |
| 4,357,497 | 11/1982 | Hochmair et al. | 607/66 X |
| 5,000,194 | 3/1991 | Van den Honest et al. | 607/137 |
| 5,545,219 | 8/1996 | Kuzma | 607/137 X |
| 5,571,148 | 11/1996 | Loeb et al. | 607/57 |
| 5,578,084 | 11/1996 | Kuzma et al. | 607/137 X |
| 5,645,585 | 7/1997 | Kuzma | 607/137 X |
| 5,649,970 | 7/1997 | Loeb et al. | 607/57 |

FOREIGN PATENT DOCUMENTS

| 28 23 798 | 9/1979 | Germany | 607/57 |
| 89/00870 | 2/1989 | WIPO | 623/10 |

Primary Examiner—Michael S. Milano
Assistant Examiner—Tram A. Nguyen
Attorney, Agent, or Firm—Bromberg & Sunstein LLP

[57] ABSTRACT

A hearing prosthesis is provided for implantation into a subject that includes a flexible electrode carrier for insertion along the length of the cochlea, the electrode carrier bearing along its length, a number of contact members that are superficially placed in pairs, each member of each pairs being diametrically opposite the other. A method of manufacture of the prosthesis is further provided.

27 Claims, 5 Drawing Sheets

STRUCTURE, METHOD OF USE, AND METHOD OF MANUFACTURE OF AN IMPLANTED HEARING PROSTHESIS

CROSS REFERENCE

This application claims the benefit of the earlier filing date of U.S. provisional patent application Ser. No. 60/012,261, filed Feb. 26, 1996 herein incorporated by reference.

TECHNICAL FIELD

The present invention relates to the structure, method of use and method of manufacture of an implanted hearing prosthesis.

BACKGROUND OF THE INVENTION

Sounds are transmitted through the outer ear to the eardrum which moves the bones of the middle ear and excites the cochlea. The cochlea is a long narrow duct wound spirally about its axis for approximately two and a half turns. The fluid filled cochlea transmit waves in response to received sounds and in cooperation with the cochlear duct, function as a transducer to generate electric impulses which are transmitted to the cochlear nerves and thence to the brain.

In people with total sensorineural hearing loss, the cochlea does not respond to sound waves to generate electrical signals for transmission to the cochleal nerves. An auditory prosthesis for the deaf therefore requires a suitable stimulation electrode capable of stimulating the auditory nerves. A design of an implantable hearing prosthesis that is currently available for use in patients includes a transmitter, a receiver and an external battery such that the receiver interacts with electrodes placed surgically in the cochlea (Hochmair et al., U.S. Pat. No. 4,284,856 and 4,357,497) so as to selectively stimulate the wall of the cochlea in accordance with the frequency response thereof. The electrodes are typically contained in an electrode carrier that is circular in cross-section and made of a flexible material but is of sufficient stiffness to be guided into the cochlea in the desired coiled shape (Hochmair-Desoyer et al., *Annals of the New York Academy of Sciences* 405:173–182 (1991)).

In 1980, Hochmair-Desoyer et al. (*IEEE Transactions on Biomedical Engineering* 27:44) described a basic electrode design that remains the accepted format. A flexible eight channel scala typani electrode carrier was developed which was circular in cross section and tapered slightly to the tip, having a diameter at each contact site along its length that was slightly smaller then the smallest diameter observed at the corresponding length in human scala tympanies. The electrode carrier contained 16 Teflon-insulated 90% Pt-10% Ir wires with a diameter of 1 mil embedded in a silastic body. The contact members were arranged in two rows on opposite sides of the electrode carrier. In the original design, each wire terminated in a ball having a diameter of 0.35 mm which protruded just slightly from the electrode carrier so as to form the contact member. This protruded form of contact member was later described by Loeb et al. (1983), *Med. and Biol. Eng. and Computing* 21:241. This design of electrode carrier was capable of being placed up to 22 mm into the cochlea.

An alternative placement of the contact members is within wells on the surface of the electrode carriers where the contact member may be surrounded at the base of the well by an annulus of conducting material. Lim (1987), *Abstracts of the Tenth Midwinter Research Meeting of the Association for Research in Otolaryngology*, No 66.; Fardeau et al. (1986), EP 0183605 and Stypulkowski (U.S. Pat. No. 4,961, 434 and 5,037,497). The electrode carrier bearing the contact members in wells was described as capable of insertion to a depth of 22 mm into the cochlea. One of the problems with the latter design is that the shape of the well permitted the trapping of air bubbles during insertion, this having the effect of interfering with the transmission of signal between the contact and the targeted auditory nerve.

Yet a third approach to contact member placement was described by Clarke in the *J. Laryngology and Otology* 93:107–109 (1979), where contact members were formed from 0.3 mm wide rings of platinum encircling the electrode carrier. The prosthesis described by Clarke was inserted up to 20 mm into the cochlea but insertion was restricted by the rigidity of the device that resulted from the spaced platinum collars along the length of the electrode carrier. Furthermore, only a minor portion of the electrical current released at the contact site could reach an auditory nerve because the current would be released over an arc of 360° to achieve contact with a neuron positioned at one site only in the arc. Consequently, the device of Clark was relatively energy inefficient.

In summary, existing implantable hearing prosthetic devices have limitations such as those listed below which it would be desirable to overcome so as to obtain a device for insertion in the cochlea that is safe, pain-free and cost effective. These limiting factors, include;

(a) The distance into the cochlea that existing prosthetic devices can penetrate without damaging the basilar partition or the bony spiral lamina. The cochlea is 34 mm in length with the auditory nerves arranged in contact with the cochleal wall in such a way as to capture low pitch sounds at the opening of the canal and high pitch sounds at the far end of the canal. Existing electrode carriers are unable to penetrate greater than about 22 mm into the cochlea. The limiting factors include the friction of the electrode carrier against the cochlea and the overall flexibility versus rigidity of the electrode carrier. The limitations of penetration inherent in existing electrode structures prevent the optimal exploitation of auditory nerves arrayed along the length of the cochlea, necessary for faithful reproduction of a sound. There is a need therefore to develop an electrode carrier capable of insertion along the entire length of the cochlea canal.

(b) The ability to accommodate the variable structure of the cochlea of individual patients in the manufacture of the device. Different patients have cochlea that are foreshortened due to various amounts of ossification of the canals. As a result, a standard electrode carrier is not optimal for all patients. There is therefore a need for a flexible system of manufacture that permits an electrode carrier of optimal length for an individual patient to be made in which the contacts are evenly spaced along the length of the electrode carrier in such a manner as to fully utilize the auditory nerves that are accessible through the length of the cochlea.

(c) The geometry of the placement of the contact members relative to the auditory nerves. An electrode carrier in the cochlea should be of a geometry enabling the surgeon to place contacts as near to the excitable nerve structures as possible. Furthermore, neurons are located on one side of the cochlea only. In the electrode carriers of the prior art which are cylindrical, there is no suggestion or teaching regarding how to localize the position of the contact members in the cochlea so as to minimize the current necessary to provide for the efficient delivery of electrical stimuli to the neurons.

There is a need therefore to develop an electrode carrier having contact members that can be located more closely to the neurons.

(d) The accurate determination of the functioning of inserted devices. Back telemetry is used to measure electrode impedances in installed electrodes. When air bubbles are formed, during insertion of the prosthetic device, impedance measurements are abnormal. With existing devices, it is not possible to determine whether an incorrect electrode impedance is due to an air bubble or to a malfunctioning contact. Incorrect impedance readings result in removal of the tested electrode carrier and possible discarding of the device and the repeat implantation of a second electrode carrier.

SUMMARY OF THE INVENTION

The invention satisfies the above needs. A novel implantable hearing prosthesis, method of use and method of manufacture are provided.

In a preferred embodiment of the invention, a hearing prosthesis for implantation into a subject has been developed that includes a flexible electrode carrier adapted for insertion into the cochlea of the ear. The electrode carrier has an oval cross-section, the cross section having a long axis. The carrier also has a plurality of discrete shaped contact member pairs arranged at a predetermined spacing along a fraction of the length of the electrode carrier. Each contact member pair is superficially placed on the carrier and comprises a first contact member diametrically opposed to a second contact member on the long axis of the cross-section.

In further embodiments of the invention, each contact member has a base portion and an extended portion, wherein the base portion is embedded within the electrode carrier, the extended portion having a top that is substantially continuous with the exterior surface of the electrode carrier. Alternatively, the contact member may be placed within wells located diametrically opposite on the long axis of the cross section and the contact member in such well may further contain an expandable extension component that may be caused to expand within the cochlea, thereby causing the contact member to be approximately placed in close contact with an auditory nerve.

A further embodiment of the invention is a method for producing a prosthesis, that includes forming a flexible electrode carrier adapted for insertion into the cochlea of the ear, the electrode carrier having an oval cross-section, the cross-section having a long axis; and placing a plurality of discrete shaped contact member pairs at a predetermined spacing along a fraction of the length of the electrode carrier, causing each contact member pair to be superficially placed on the carrier and comprising a first contact member diametrically opposed to a second contact member on the long axis of the cross-section.

A further embodiment of the invention is a method for implanting a hearing prosthesis in a subject that includes selecting a flexible electrode carrier adapted for insertion into a cochlea, the electrode carrier being oval in cross section; and having a plurality of discrete shaped contact member pairs along the surface of the electrode carrier, each contact member pair having a first and a second contact member such that the first contact member is diametrically opposed to the second contact member on the cross-sectional long axis, and inserting the flexible electrode carrier into the cochlea so that one contact member in each pair is adjacent to at least one auditory nerve.

A further embodiment of the invention is a method for manufacturing an individually customized implantable hearing device for a subject that includes measuring the evoked auditory nerve potential of the cochlea; determining the location and density of responsive neurons; and preparing an electrode carrier as described above, having suitably placed contact members.

BRIEF DESCRIPTION OF THE DRAWINGS

These and other features, aspects and advantages of the present invention will become better understood with reference to the following description, appended claims and accompanying drawings where

FIG. 4 (*a*)–(*c*) show three separate cross sectional views of the electrode carrier during manufacture where the electrode carrier is placed in a mold having 8 pairs of vacuum holes spaced regularly over different lengths along the electrode channel for placing the contact members.

FIG. 5 shows an outline of the oval cross section of an electrode carrier with the marked location of contact members.

DETAILED DESCRIPTION OF SPECIFIC EMBODIMENTS

Definition of terms

An electrode carrier is defined here and in the claims as the body of the implantable device.

A contact member is defined here and in the claims as the terminal component of the electrode.

Figure 4A:
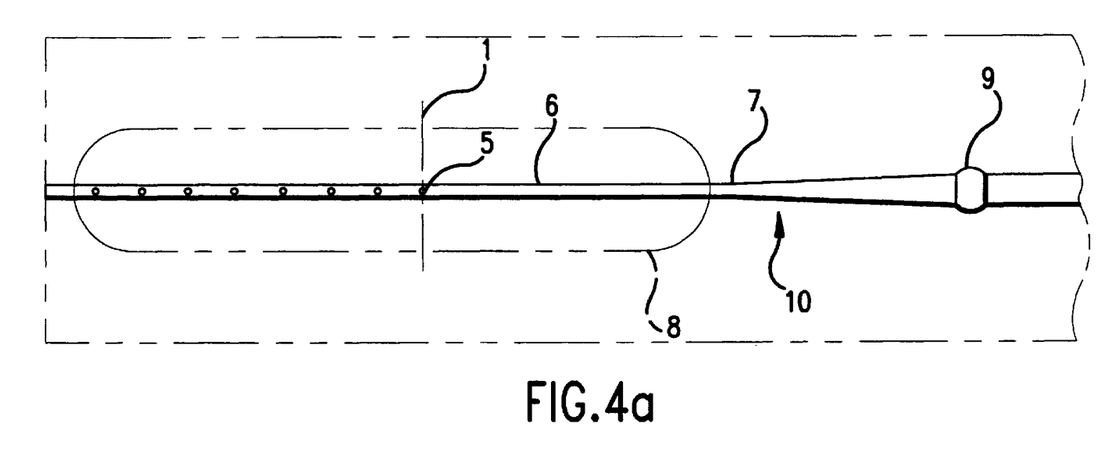
Figure 4B:
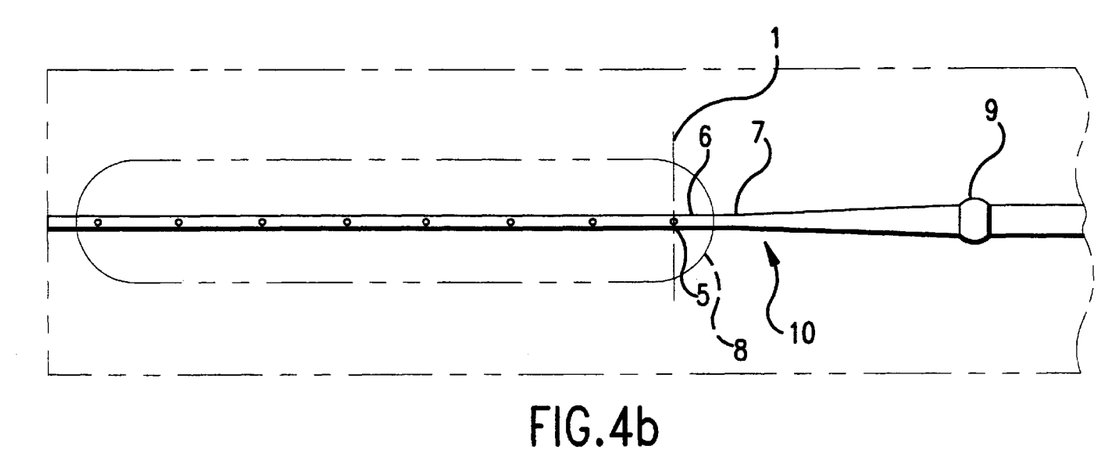
Figure 4C:
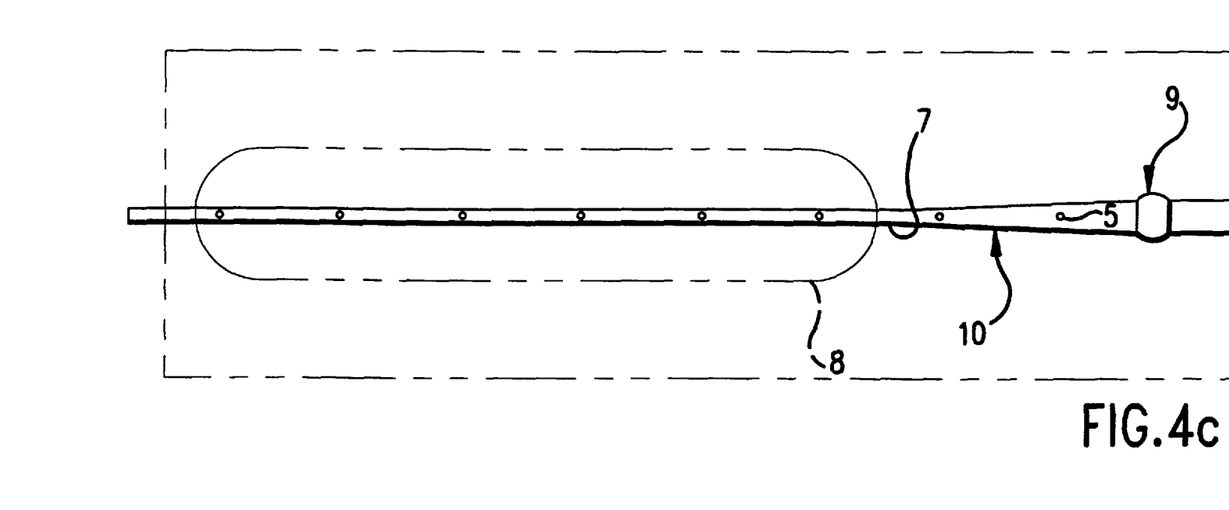

An electrode carrier has been designed as shown in FIGS. 4(*a*)–(*c*). The electrode bears a marker (9) at a predetermined distance from the tip of the electrode carrier to delimit the region of the carrier that should not be contacted by the surgeon during placement of the prosthesis. From the marker, toward the tip of the electrode carrier, the diameter of the electrode carrier tapers to about 1.5 mm at (10). The distance between (10) and (9) and the relative increase in diameter as well as precise location of the marker directly impact the formation of kinks in the electrode during implantation. It is desirable to limit the occurrence of such kinks. In one embodiment of the invention, the marker is located at a distance of about 10 mm from the closest contact member and has a diameter of approximately 3–4 mm. The minimum diameter of the electrode carrier is 1–2 mm or more particularly 1.5 mm in this embodiment, increasing in diameter to about 3–4 mm (more particularly 3 mm)over a distance of about 3–5 mm (more particularly 3.5 mm). Where the electrode carrier is oval in cross-section, equivalent minimum values for the diameter along the short axis (12) and the long axis (11) may be selected to maximise the depth of insertion.

Contained within the electrode carrier is a series of wires that terminate, at selected sites on the surface of the carrier, to form contact members. In a preferred embodiment of the invention, the wire (Pt-Ir(25%)) has a 25 $\mu$m diameter with a 5 $\mu$m Teflon insulation layer. The thickness of the wire is approximately inversely related to the flexibility of the electrode carrier so that a thick wire causes the electrode carrier to be less flexible then it would be otherwise.

The electrode carrier is formed from a polymer having a flexibility profile that is sufficient to permit the placement of the carrier at a distance greater than 24 mm into the cochlea. In one embodiment of the invention, a silicon elastomer is used that is supplied by Applied Silicon in California and is called Silastic LSR40 having.

The wires within the electrode carrier are attached to contact members that are placed at selected locations along the electrode carrier as shown in FIG. 4.

The contact members are orientated on the surface of the electrode carrier so as to maximize the proximity of each contact member with neurons. This is further accomplished by any or all of the considerations itemized below:

maximizing the penetration length of the electrode carrier within the cochlea of individual patients, the maximum length being 34 mm, the entire length of the cochlea itself. The optimum maximum length may vary according to the differing amounts of ossification of the cochlea as well as the location of the functioning neurons;

introducing flexibility in the design of the electrode carrier to accommodate inter-patient variability in the extent of functioning neurons in the cochlea; and selecting a cross sectional shape of the electrode carrier such that at least one contact member in each pair is located adjacent to the functioning neurons.

an advantage of utilizing the maximum length of the cochlea includes access to locations where the induced pitch percept corresponds to the pitch percept naturally elicited in the normal hearing person by an incoming sound of the frequency which is the "best" frequency. The "best" frequency is here defined as the frequency for which the tuning curve of single auditory nerve fibers, the threshold of hearing for an acoustic signal, is lowest. In this manner, naturally sounding hearing sensations can be obtained and the length of period of increasing speech perception until saturation is reached will be shorter.

To maximize the depth of insertion of the electrode carrier, it is desirable to form an electrode carrier having a continuous surface to minimize friction and to reduce the incidence of air bubbles.

In an embodiment of the invention, the electrode carrier is oval in cross-section thereby having a long axis on which contact member pairs placed in a diametrically opposed position. The oval cross-section of the electrode carrier provides a means for introducing the prosthetic device in a single orientation such that the contact members are always located in a north and south position on the oval perimeter. Furthermore, the electrode carrier having this shape may not twist during insertion in contrast to the circular designed electrode carriers of the prior art. In an embodiment of the invention, the contact members may be located as described above in a north and south orientation on the long axis of the oval electrode carrier within wells, the wells optionally containing an expandable extension of the contact member. The expandable extension may be positioned in a well such that when the electrode carrier is placed in the cochlea, the contact member becomes raised so as to be approximately touching the auditory nerves. The raising of the contact members in an expandable extension may be accomplished for example, by osmosis or by the hydration of a polymer. The expanded component may be finger-like in shape. One advantage of increasing the proximity of a contact member to the auditory nerve is to improve sound reproduction. Another advantage is the improved focus of stimulatory current and hence a reduction in the amount of current required to obtain a beneficial effect. This in turn has a beneficial effect on reducing the size and increasing the longevity of the external battery power source.

A further embodiment of the invention directed to increasing the proximity of the contact member to the nerve in the cochlea is to determine the location and activity of nerves in the patient prior to implantation of the prosthesis. This may be achieved by using evoked auditory nerve potential or compound action potential to identify the site of active neurons in the patient's cochlea.

Once the prosthesis device is in place, the effective stimulation of auditory nerves by the contact member could be established by a comparison of evoked potential before and after insertion of the device.

Manufacture and Placement of Contact Members

Figure 1A:
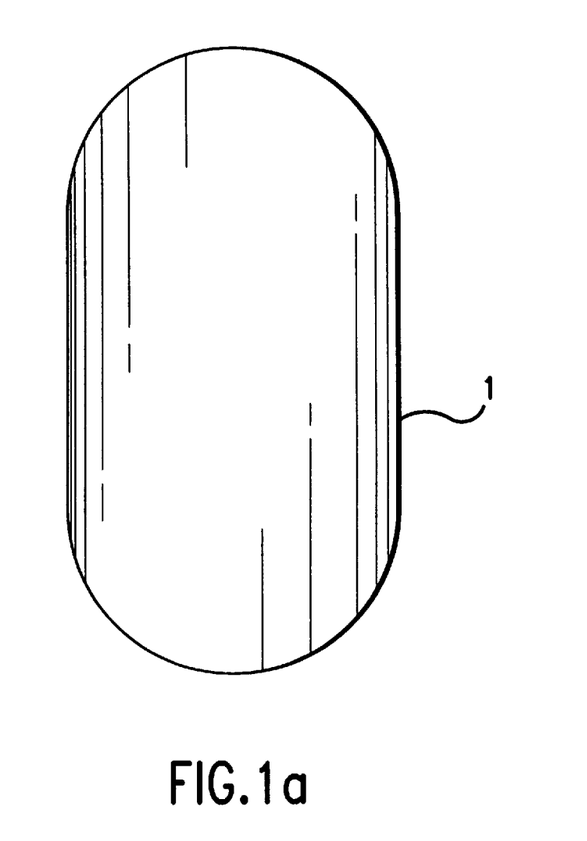
FIG. 1*a* is a top view of a metal foil that has been pressed out of a larger sheet in a semi-oval shape.
Figure 1B:
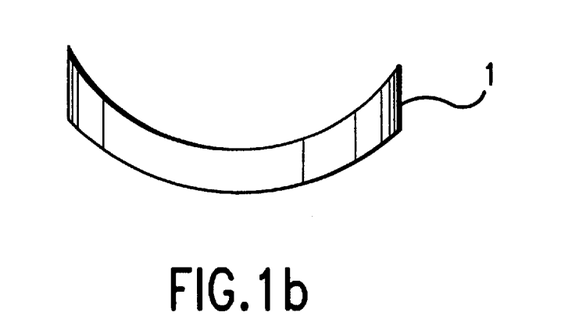
FIG. 1*b* shows a cross section through the metal foil.
Figure 2A:
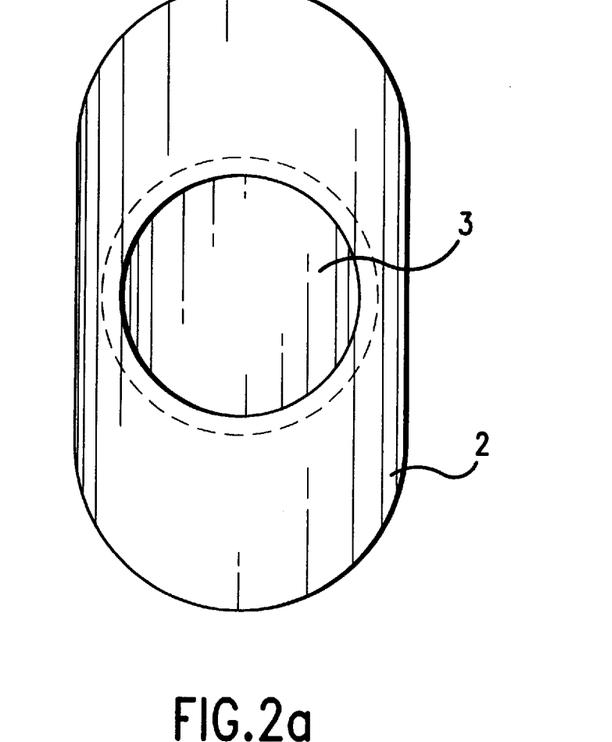
FIG. 2*a* is a top view of the metal foil after molding into a hat shape while 2*b* shows a cross section through the contact member.
Figure 2B:
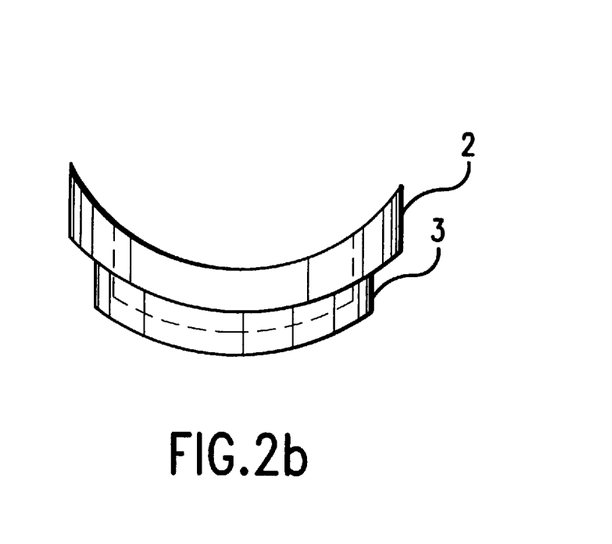
Figure 3:
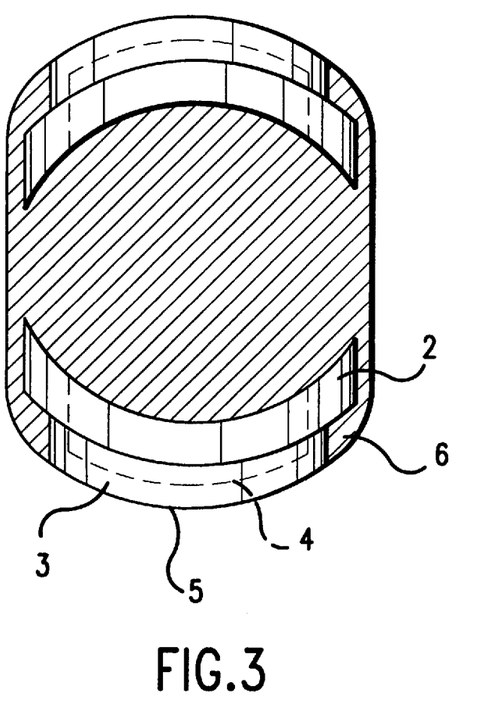
FIG. 3 is a cross-section through the electrode carrier (along lines III—III shown in FIG. 4(*a*) below) showing the placement of two opposing contacts on the long axis.

FIGS. 1–3 describe embodiments of the manufacture and placement of contact members in the electrode carrier. In FIG. 1a, an oval piece (1) is punched out of a sheet of foil. This punched out form has a thickness of 0.5 mm and a radius of curvature of 0.3 mm (FIG. 1b). FIG. 2a shows the oval piece of metal foil after it has been pressed over a mold, where the mold imposes a shape on the foil which includes a base portion (2) and an extended portion (3) such as exemplified by a hat-shape, where the base portion has a larger perimeter then the extended portion. The extended portion may be symmetrically disposed above the base portion as shown in FIG. 2(a) although the extended portion may alternatively be asymmetrically placed on the base portion in certain embodiments. The base portion may have a similar or equal radius of curvature to the extended portion and may also have a similar or equal thickness to the extended portion. FIG. 3 shows the orientation of the contact member in the electrode carrier. The base portion (2) is embodied within the polymer of the electrode carrier and the surface of the extended portion (5) is substantially continuous with the surface of the electrode carrier (6). According to FIGS. 2b and 3, the extended portion is hollow where the cavity (4) extends through the base portion.

FIGS. 4(a)–(c) show the alignment of eight contact members pairs along the length of the electrode carrier (7) [(A), (B) and (C)] such that the distance between each contact is varied according to the overall length of the electrode carrier. For example in (A), each contact surface (5) is placed at a distance of 1.6 mm from the adjacent contact member, where the electrode carrier is 22.2 mm in length. In (B), each contact member surface is placed at a distance of 2.8 mm from the adjacent contact, where the electrode carrier is 30.8 mm in length. In (C), each contact surface is placed at a distance of 3.80 mm from the adjacent contact member, where the electrode carrier is 30.76 mm in length.

In further embodiments of the invention, the number of pairs of contact members may vary according to the condition of the cochlea. For example, electrode carriers may have 4, 5, 6, 7, 9, 10, 11, 12, or more pairs of contact members, for example in a range of 4–16 pairs of contact members. Furthermore, the distance between adjacent pairs of contact members may vary according to the number of pairs of contact members located on the electrode carrier and the condition of the cochlea in the subject.

In a preferred embodiment, the cross section of the electrode carrier as shown in FIG. 3, may be elliptical or oval in shape. The oval shaped cross-section of the carrier facilitates the insertion of the electrode carrier into the cochleal canal by permitting increased bending of the electrode carrier along the short axis of the cross section. The consistent orientation of the oval electrode carrier is not possible with the cylindrical electrodes of the prior art.

Furthermore, the contact members are placed in pairs along the electrode carrier such that one contact member in the pair is placed at a location on the surface of the carrier that is opposite to the surface location of the second contact member in the pair on the long axis. This arrangement permits at least one contact member to be adjacent to the nerves to be stimulated. This improved localization of the contact with regard to the auditory nerves makes possible the focussed delivery of current through a relatively small arc and thereby requires a reduced threshold of current required to stimulate the nerves. The advantages of reduced stimulatory current requirements is apparent in the reduced size and increased longevity of the battery that accompanies the prosthesis.

Manufacture of the Electrode Carrier

A mold (8) is used as shown in FIG. 5, which is formed of two halves that are mirror images of each other. The mold has fenestra along its' length to which vacuum lines are connected (9). The metal foil contact as shown in FIG. 2 *a* and *b* are placed into the fenestra in each mold half under vacuum. The electrodes to be connected to the contact members are placed within a longitudinal hollow cavity in the mold and a single electrode wire is positioned over each fenestra and joined to the metal foil contact. The two mold halves are then put together and injected with a polymer (preferably a silicon elastomer such as Silastic LSR 40 The stiffness of the polymer is selected to provide sufficient flexibility necessary for insertion of the electrode carrier into the cochleal canal at a depth in the range of up to 32 mm.

All of the above cited references and publications are hereby incorporated by reference.

Those skilled in the art will recognize, or be able to ascertain using no more than routine experimentation, equivalents to the specific embodiments of the invention described herein. Such equivalents are intended to be encompassed by the following claims.

We claim:

1. A hearing prosthesis for implantation into a subject, comprising:
   (a) a flexible electrode carrier adapted for insertion into a cochlea, the electrode carrier having an oval cross-section, the oval cross-section having a long axis; and
   (b) a plurality of discrete shaped contact member pairs arranged at a predetermined spacing along a fraction of the length of the electrode carrier, wherein each contact member pair is superficially placed on the carrier and comprises a first contact member diametrically opposed to a second contact member on the long axis of the cross-section.

2. A prosthesis according to claim 1, wherein each contact member is superficially located within a recess at the surface of the electrode carrier.

3. A prosthesis according to claim 1, wherein each discrete shaped contact member has an extension component.

4. A prosthesis according to claim 3, wherein the extension component expands within the cochlea to achieve closer proximity to a neuron after expansion than before expansion.

5. A prosthesis according to claim 4, wherein the expanded extension component is finger-shaped.

6. A prosthesis according to claim 1, wherein each discrete shaped contact member is substantially continuous with the exterior surface of the electrode carrier.

7. A prosthesis according to claim 6, wherein each discrete shaped contact member has a base portion and an extended portion, wherein the base portion is embedded within the electrode carrier, the extended portion having a top that is substantially continuous with the exterior surface of the electrode carrier.

8. A prosthesis according to claim 7, wherein the extended portion is symmetrically disposed above the base portion.

9. A prosthesis according to claim 8, wherein each contact member includes two curved discs having different sizes, such that a portion of the smaller disc is substantially continuous with the exterior surface of the electrode carrier.

10. A prosthesis according to claim 1, wherein each contact member is formed from a metal foil.

11. A prosthesis according to claim 1, wherein the flexible electrode carrier comprises an electrode channel molded within a flexible polymer connected with a plurality of contact members, wherein the flexible electrode carrier is capable of achieving penetration of up to 32 mm into the cochlea.

12. A prosthesis according to claim 1, wherein the spacing between the plurality of contact members is varied according to the final length of the electrode carrier so as to optimize the stimulation of the auditory nerves at a selected pitch in the subject.

13. A prosthesis according to claim 1, wherein the plurality of contact members is in the range of 4–16 pairs of contact members.

14. A method for manufacturing an individually customized implantable hearing device for a subject, comprising;
   measuring the evoked auditory nerve potential of the cochlea;
   determining the location and density of responsive neurons; and
   preparing an electrode carrier as described in claim 13, having suitably placed contact members.

15. A method for producing a prosthesis, comprising:
   (a) forming a flexible electrode carrier adapted for insertion into a cochlea, the electrode carrier having an oval cross-section, the cross-section having a long axis; and
   (b) placing a plurality of discrete shaped contact member pairs at a predetermined spacing along a fraction of the length of the electrode carrier, causing each contact member pair to be superficially placed on the carrier and comprising a first contact member diametrically opposed to a second contact member on the long axis of the cross-section.

16. A method according to claim 15, wherein step (b) further comprises placing each contact member within a recess at the surface of the electrode carrier.

17. A method according to claim 15, wherein each shaped contact member further comprises an extension component.

18. A method according to claim 17, wherein step (b) further comprises expanding the extension component within the cochlea to achieve closer proximity to a neuron after expansion than before expansion.

19. A method according to claim 15, wherein step (b) further comprises causing the surface of each contact member to be shaped and positioned so as to be substantially continuous with the exterior surface of the electrode carrier.

20. A method according to claim 19, further comprising shaping each contact member so as to have a base portion and an extended portion; and
   embedding the base portion within the electrode carrier, the extended portion having a top that is substantially continuous with the exterior surface of the electrode carrier.

21. A method according to claim 20, further comprising symmetrically disposing the extended portion above the base portion.

22. A method according to claim 21, wherein each contact member includes two curved discs having different sizes, such that a portion of the smaller disc is substantially continuous with the exterior surface of the electrode carrier.

23. A method according to claim 15, further comprising forming each contact member from a metal foil.

24. A method according to claim 23, further comprising forming the electrode carrier from a material including a flexible polymer.

25. A method according to claim 15, further comprising, varying the spacing between each pair of contact members according to the final length of the electrode carrier for optimizing the stimulation of auditory nerves at a selected pitch and amplitude.

26. A method according to claim 15, wherein the plurality of contact members is in the range of 4–16 pairs of contact members.

27. A method for implanting a hearing prosthesis in a subject, comprising:

selecting a flexible electrode carrier adapted for insertion into a cochlea, the electrode carrier being oval in cross section; and having a plurality of discrete shaped contact member pairs along the surface of the electrode carrier, each contact member pair having a first and a second contact member such that the first contact member is diametrically opposed to the second contact member on the cross-sectional long axis; and inserting the flexible electrode carrier into the cochlea so that one contact member in each pair is adjacent to at least one auditory nerve.

* * * * *